United States Patent [19]

Haluska et al.

[11] Patent Number: 4,472,464
[45] Date of Patent: Sep. 18, 1984

[54] TINTABLE, DYEABLE, CURABLE COATINGS AND COATED ARTICLES

[75] Inventors: Loren A. Haluska; Marcelle G. Molzahn, both of Midland, Mich.

[73] Assignee: Dow Corning Corporation, Midland, Mich.

[21] Appl. No.: 484,761

[22] Filed: Apr. 14, 1983

Related U.S. Application Data

[62] Division of Ser. No. 340,160, Jan. 18, 1982, Pat. No. 4,421,893.

[51] Int. Cl.$^3$ .............................................. B05D 3/02
[52] U.S. Cl. ................................... 427/387; 428/447; 524/588; 524/493; 524/847; 524/430; 524/858; 524/859; 528/16; 528/17; 528/29; 528/33; 525/102; 525/105; 525/477; 556/414; 556/419; 556/421; 556/424; 556/427
[58] Field of Search .................... 525/102, 105, 477; 528/16, 17, 29, 33; 524/588, 847, 493, 430, 858, 859; 556/414, 419, 421, 424, 427; 427/387; 428/447

[56] References Cited

U.S. PATENT DOCUMENTS

| | | | |
|---|---|---|---|
| 3,986,997 | 10/1976 | Clark | 428/412 |
| 4,073,967 | 2/1978 | Sandvig | 428/422 |
| 4,088,670 | 5/1978 | Bargain et al. | 556/414 |
| 4,211,823 | 7/1980 | Suzuki et al. | 428/412 |

*Primary Examiner*—Melvyn I. Marquis
*Attorney, Agent, or Firm*—Robert L. McKellar

[57] ABSTRACT

The invention disclosed in this application is the use of novel silanes in curable coatings to allow tinting or dyeing of the coatings after they are cured on certain substrates.

An example of one such useful silane is

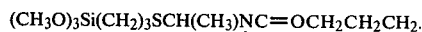

$(CH_3O)_3Si(CH_2)_3SCH(CH_3)NC=OCH_2CH_2CH_2$.

The silanes and the curable coatings are also useful as antistat and antifog coatings.

6 Claims, No Drawings

TINTABLE, DYEABLE, CURABLE COATINGS AND COATED ARTICLES

BACKGROUND OF THE INVENTION

This application is a divisional of Ser. No. 340,160, filed Jan. 18, 1982, now U.S. Pat. No. 4,421,893.

The present invention relates to coating compositions which are curable and which can be used on transparent solid substrates. These coating compositions contain novel silanes which allow for dyeing and/or tinting (hereinafter "tintability") of such solid substrates. The curable coating compositions, containing the novel silanes, not only allow tintability, but these coating compositions also give excellent abrasion resistance, antifog and antistat properties to the coated article. In addition, the coatings described herein give very aesthetically pleasing, uniform, gel-free surfaces to the coated article.

Plastic materials, especially clear, transparent plastic materials, have been used in increasing amounts for various applications where the user desired such properties as lightweightness and ease of handling. Further, plastics have been developed which are not only lightweight but are strong such that they have application in those uses where breaking, cracking or splintering are a problem, such as in eyewear. In the United States in 1977, the sales of glass spectacle lenses was estimated at about 40 million pairs as opposed to about 21 million pairs for plastic. It is predicted that in 1982, 30 million pairs of glass lenses will be sold as compared to 40 million pair of plastic lenses.

A certain number of these lenses will be tinted in order to reduce the transmission of light through them. This tintability of the lenses does not seem to be a major problem, since there are a number of tints of varying colors which can be used to tint the lenses. Moreover, the plastics are readily receptive to these tints so that various intensities, as well as various colors of lenses, can be obtained.

Plastic substrates have several major problems, however. Generally, polycarbonates and acrylics are soft, and articles prepared from these plastics scratch or abrade quite readily. Therefore, there has been a great deal of investigation into coatings for such articles in order to enhance the abrasion resistance of the surface of the plastic articles. This problem is particularly acute in plastic lenses and transparent plastic sheeting used in bus, airplane, and train windows and in architectural windows and panels.

One premier coating that has found wide acceptance for such applications is the coating known as the Dow Corning abrasion resistant coating, which is a siloxane based, silica reacted, curable coating especially adapted to give hard surfaces when cured on plastic substrates. This material is disclosed in U.S. Pat. No. 3,986,997, issued Oct. 19, 1976. This material, however, even though having a hard, abrasion resistant surface, has a major drawback. It is not tintable! Therefore, it would be useful to develop an abrasion resistant coating which not only gave enhanced abrasion resistance to these plastic substrates, but it would be extremely useful if the coating was also tintable.

Such coatings have been developed, but they too have some drawbacks. For example, U.S. Pat. No. 4,211,823, issued July 8, 1980, describes the preparation of a tintable coating for use on plastic substrates. The material comprises a hydrolyzate of a silane compound containing at least one epoxy group and not less than two alkoxy groups, fine silica particles and an aluminum chelate compound. This material is tintable but suffers from the fact that it is not exceptionally abrasion resistant, and it has a short resin pot life with a tendency to easily form gel specks.

Another coating system for use on lenses is a material described in U.S. Pat. No. 4,073,967, issued Feb. 14, 1978, as a combination of a reactive silane and a metal cluster. This material is tintable but does not offer the ultimate in abrasion resistance and handleability.

Furthermore, it would be desirable to have an additive for various resins in order to achieve tintability in resins which are not themselves ordinarily tintable.

The silane adducts of this invention help overcome the problems associated with the prior art materials and, in addition, these silane adducts are not volatile under coating curing conditions or in use in the cured coating. As long as the silane adducts are compatible with the curable resin, the adduct will be useful and perform its function therein.

THE INVENTION

This invention therefore deals with a composition of matter which is a silane having the general formula (XO)$_3$SiRSR' wherein X is an alkyl radical of 1-4 carbon atoms, R is a divalent aliphatic hydrocarbon radical containing less than five carbon atoms and R' is selected from a group consisting of

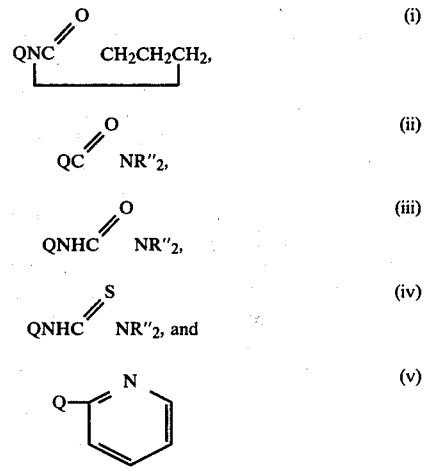

wherein Q is a radical selected from a group consisting of —CH$_2$CH$_2$—, —CH$_2$CH$_2$CH$_2$—,

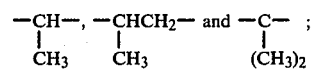

wherein in groups (iii), and (iv), R" is hydrogen or the methyl group and in group (ii), R" is hydrogen, the methyl group or the isobutoxymethyl group.

In this invention, X is an alkyl radical of 1-4 carbon atoms, and examples of such radicals include the methoxy, ethoxy, propoxy and butoxy radicals. It should be noted that there are always three such groups per molecule. It is believed that the presence of these groups allows for the non-volatility of the compound when heated during the cure reaction or when the cured coating is subjected to extreme temperatures when in use.

R for purposes of this invention is a divalent aliphatic hydrocarbon radical containing less than five carbon atoms. The alkylene bridge in these silanes should be as small as possible, as the increased molecular size leads to the loss of abrasion resistance in the final cured resin. Therefore, the alkylene bridge is preferred to be three carbons or less in length. Thus, methylene, ethylene and propylene radicals are the preferred alkylene bridges in this invention. Most preferred is the propylene bridge because of the simplicity of manufacturing the silanes using the propylene bridge precursor, i.e. the allyl group.

The letter S is a sulfur atom and R' is selected from a very narrow group as set forth in the specification above as groups (i)–(v). Q in these groups is a radical selected from a group consisting of —CH$_2$CH$_2$—, —CH$_2$CH$_2$CH$_2$—,

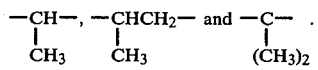

R" in these groups takes on a different meaning depending on which group, (ii), (iii) or (iv), is being considered. In groups (iii) and (iv), R" can be hydrogen or the methyl group, and in group (ii), R" can be hydrogen, the methyl group or the isobutoxymethyl group. No such groups are shown as required for groups (i) or (v) because of the nature of the molecules.

The limitations on these groups, R", is only because of the unavailability of the precursor compounds.

There are a number of methods by which these materials can be produced. It is known, for example, to add mercaptan groups to unsaturated organic groups under the influence of free radical catalysts or ultraviolet light. Thus, one can prepare these compounds by adding mercaptoalkyl-containing trialkoxy silanes to unsaturated organic amines and amides or, one can add mercapto containing organoamines or amides to unsaturated trialkoxysilanes. Conventional free radical catalysts or ultraviolet light will cause such reactions to be efficient; however, sometimes added catalysts are not necessarily required for these reactions. Sometimes solvents can be used, but they are not required in some cases. Generally, the materials to be reacted are mixed together and then catalyzed and then gently heated. Quite frequently, after gentle heating, the reaction exotherms to near completion of the reaction. Occasionally, the reaction is required to be refluxed for a period of time to ensure the completion of the addition reaction.

The preferred method for this invention is the addition of commercially available mercaptoalkyl-containing trialkoxysilanes to unsaturated organic amines or amides under the influence of peroxides or azobisisobutyronitrile catalysts. The unsaturation on the organic precursors is preferred to be the allyl or vinyl groups.

The examples clearly illustrate the methods and means preferred for the manufacture of the inventive silanes herein.

A further aspect of this invention is the use of the above-mentioned silanes as additives to curable resins. This invention therefore also consists of a composition of matter which comprises (A) 1 to 50 weight percent, based on the weight of (A) and (B), of a silane having the general formula (XO)$_3$SiRSR' wherein X is an alkyl radical of 1 to 4 carbon atoms, R is a divalent aliphatic hydrocarbon radical containing less than five carbon atoms and R' is selected from a group consisting of

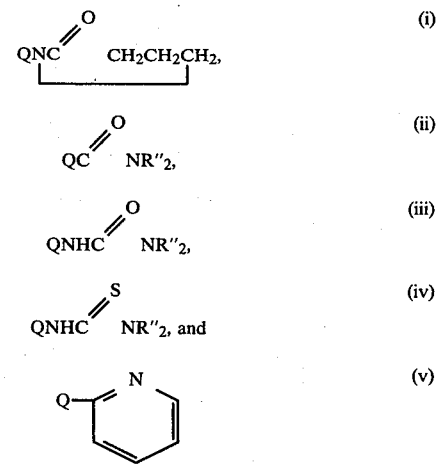

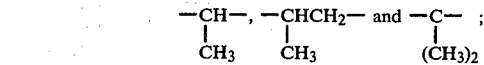

wherein Q is a radical selected from a group consisting of —CH$_2$CH$_2$—, —CH$_2$CH$_2$CH$_2$—, $$-\underset{\underset{CH_3}{|}}{CH}-, \quad -\underset{\underset{CH_3}{|}}{CH}CH_2- \quad \text{and} \quad -\underset{\underset{(CH_3)_2}{|}}{C}-\;;$$

wherein in groups (iii) and (iv), R" is hydrogen or the methyl group and in group (ii), R" is hydrogen, the methyl group or the isobutoxymethyl group and (B) 99 to 50 weight percent, based on the weight of (A) and (B), of a curable resin compatible with component (A).

The curable resin and the silane additive must be compatible in order for the additive to function as it should, to give uniform tintability. Generally, from 1 to 50 weight percent of silane (A), based on the total weight of (A) and (B), will work properly in this invention. Generally, as the weight percent of the additive in the composition increases, the intensity of the tint increases. Also, as the weight percent of the additive in the composition increases, the abrasion resistance decreases. The abrasion resistance will decrease nominally at the lower amounts of additive, i.e., 1–25 weight percent, then the abrasion resistance will decrease dramatically with larger quantities of additive. The loss of abrasion resistance is dependent on the curable resin used and the amount of additive used in that resin. Normally, 15–35 weight percent of the additive gives the best tintability and the least amount of loss in abrasion resistance.

The additive is useful in any curable resin in which it is compatible.

Since the additive is a silane, it is quite compatible with silicone-based resins or silicone-organic resins. It is least compatible with organic resins. The additive is highly compatible with the resins described in U.S. Pat. Nos. 4,073,967, 4,211,823 and 3,986,997, and wide variations of such pigment-free coating compositions. Especially good resins, which are highly compatible with the additives of this invention, are these comprising 30 to 70 weight percent of colloidal silica; 0 to 25 weight percent of R""SiO$_{3/2}$ as a partial hydrolyzate, wherein R"" has the meaning set forth for R in U.S. Pat. No. 3,986,997 and includes also the phenyl radical and the gamma mercaptopropyl radical and 15-35 weight percent of the silane additive, all based on the total weight of colloidal silica, $R''''SiO_{3/2}$ and silane additive in the mixture. This material is similar to the compositions described in U.S. Pat. No. 3,986,997, but the relative amounts of colloidal silica and partial hydrolyzate are changed to enhance the tintability of films prepared from this resin. The amount of partial hydrolyzate can be reduced to zero if the silane additive is cohydrolyzed into the system along with the colloidal silica. Small amounts of the partial hydrolyzate can be used with the colloidal silica, that is, up to 25 weight percent of the colloidal silica/partial hydrolyzate can be partial hydrolyzate. The solvents, catalysts and adjuncts set forth in U.S. Pat. No. 3,986,997 can also be used in this resin composition.

It is possible to use solvents to enhance the compatibility of the silane additive in the resin systems. Solvents found to be useful herein are alcohols, glycols, glycol ethers, ketones and esters.

Catalysts for these resin systems are dependent on which systems are used. The presence of the silane in the resin does not appear to affect catalysis.

One further aspect of this invention is a solid substrate coated with the silane additive. Thus, the silane additive can be made curable and, in this form, it can be coated on a substrate, cured, and be tinted in the manner described in the examples.

In addition, the invention consists of solid substrates coated with the resin composition containing the silane additive. This aspect of the invention is very important because of the fact that a storage stable, one coat, tintable, curable coating is needed in the marketplace for plastic spectacle lenses and plastic windows and decorative panels.

Further, the resin compositions containing the silane additives are useful as coatings on various substrates as an antistatic coating. Thus, this material can be used on any substrate, transparent or non-transparent, if an antistatic coating is required. Further, this material can be used as an antifog coating on various substrates and, therefore, when an antifog coating is required, this material can be used.

It should be noted that the silane additive can be cured through hydrolysis and then catalysis so that the silane additive itself can be used as an antistatic and/or antifog coating.

Substrates that can be coated with the compositions of this invention include leather, plastic, wood, metal, rubber, paper and glass.

Particularly, plastic lenses, sheets and art objects can be coated. Glass windows, for example aircraft windows, can be made antifog and antistatic. Metals can be coated with these compositons, especially aluminum, which when coated with these compositions, can be tinted with various tints and dyes.

In the following examples, the apparatus and testing procedures used for the results shown therein are as follows:

Vapor Degreasing

Some of the plastic panels used herein were degreased by subjecting them to a five minute immersion in Freon TM TES (trichlorotrifluoroethane including 4% denatured ethanol and a stabilizer proprietary to DuPont, E. I. DuPont deNemours, Wilmington, Del., USA) in a Branson Ultrasonic Degreaser (Branson Cleaning Equipment Co., Shelton, CT, USA).

Heat Cleaning

After vapor degreasing, all plastic panels coated in the examples were heat annealed by subjecting the panels to at least two hours at 125° C. for polycarbonate and two hours at 80° C. for acrylic. The panels were always cooled to room temperature before coating.

Tinting Materials

All tinted samples were tinted using Sun Brown Molecular Catalytic TM dyes manufactured by Brain Power Inc., Miami, FL, USA.

The samples were tinted in a hot aqueous bath at about 85° C. for 15 minutes. The length of time of tinting when varied is noted in the examples.

Light Transmission

The amount of tintability was determined by reading the amount of light transmitted through a coated panel. The difference in light transmission before and after the tinting was taken on a Gardner ® Haze Meter, Model UX10 coupled to a P5500 Photometric Unit. The light transmission is reported in percent of total light transmitted through the sample.

Adhesion Testing

Adhesion was measured by crosscut adhesion. A series of scratches are made through the coating into the substrate in the pattern of a grid containing 25 squares, each being about 1.5 mm square (1/16 in.). This surface is covered with No. 600 Scotch Brand adhesive tape (3M C., USA) and pressed down firmly. The tape is withdrawn from the surface with one rapid motion at about a 90° angle from the surface of the substrate. The number of squares remaining intact on the substrate are reported as a percentage of the total number of squares on the grid.

Abrasion Resistance

Abrasion resistance was determined according to ASTM Method D1044-56. The instrument was a Taber Abraser. A 500 gram test load was used with CS-10F abrasive wheels and the test panels were subjected to 500 revolutions on the abraser turntable. The percent change in haze which is the criterion for determining the abrasion resistance of the coating is determined by measuring the difference in haze of the unabrased and abrased coatings. Haze is defined as the percentage of transmitted light which, in passing through the specimen, deviates from the incident beam by forward scattering. In this method, only light flux that deviates more than 2.5 degrees on the average is considered to be haze. The %Δ Haze on the coatings was determined by ASTM Method D1003-61. A Hunter Haze Meter, manufactured by Gardner Laboratory, Inc., was used The Δ Haze was calculated by measuring the amount of diffused light, dividing by the amount of transmitted light and multiplying by one hundred.

EXAMPLE 1

Preparation of

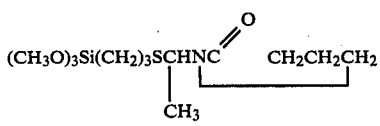

Vinylpyrrolidone, 55.6 gms. (0.5 mole) was weighed into a 500 ml., 3-necked, round-bottomed glass flask. The flask was equipped with a water-cooled condenser, stirrer, thermometer, addition funnel and gas inlet tube. Mercaptopropyltrimethoxysilane, 107.8 gms. (0.55 mole) and Vazo ® 64 catalyst (2,2'-azobis isobutyronitrile manufactured by E. I. DuPont deNemours and Co. Inc., Wilmington, Del., USA) (0.5 gm.) were mixed and placed in the addition funnel. Nitrogen flow was started to remove air from the flask and apparatus and nitrogen purge was used throughout the duration of the experiment. The flask was heated to about 82° C. and the mixture from the addition funnel was added to the flask contents which were reddish-purple in color at the beginning of the addition. The color turned to clear brown and then to clear yellow. An exotherm was observed to about 90° C. where it was controlled with an ice water bath and the flask temperature was maintained between 85°-90° C. during the reaction. The addition took place over about 1 hour. The reaction was heated for about four hours after the addition had been made. An aliquot of the reaction product was titrated using standardized iodine to show that the anticipated reaction has proceeded to greater than 96% completion. Proton NMR analysis showed a structure consistent with the title compound.

EXAMPLE 2

Preparation of

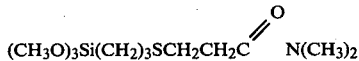

Mercaptopropyltrimethoxysilane, 107.8 gms., was weighed into a flask equipped as in Example 1, above. Vazo 64, (0.5 gm.) was added and the solution stirred to dissolve the Vazo 64. The N,N-dimethylacrylamide (NNDA) was poured into the addition funnel and the flask was heated to 80° C. The addition was begun and was accompanied by an exotherm which was controlled between 82°-90° C. The addition was made in about 20 minutes. The pot temperature was maintained for about four additional hours after the addition was complete. Iodine titration showed the reaction had proceeded to about 97% conversion. Proton NMR analysis showed the structure consistent with the title compound.

EXAMPLE 3

Preparation of

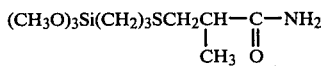

Mercaptopropyltrimethoxysilane, 100 gms. (0.5 mole) was weighed into a flask and the flask was equipped as in Example 1 above. To this was added 0.6 gm. of Vazo 64. Methacrylamide (MA) 42.6 gms. (0.5 mole) was dissolved in 150 gms. of methanol and placed in the addition funnel and added to the flask over a six-hour period while the flask was heated and maintained at about 85° C. The heat was shut down and the remainder of the addition was carried out over a 14–16 hour period. A small amount of Vazo 64 was added to the flask and reheating was started and the temperature was taken to about 100° C. and held for about six hours. Another small amount of Vazo 64 was added and the temperature was raised to 105° C. for an additional seven hours. The reaction had proceeded about 86% as indicated by an iodine titration. The H'NMR analysis is consistent with the structure $(CH_3O)_3Si(CH_3)_3SCH_2CH(CH_3)C=ONH_2$.

EXAMPLE 4

Preparation of

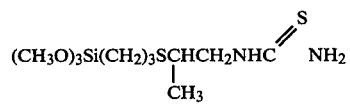

Mercaptopropyltrimethoxysilane, 92 gms. was placed in a 500 ml flask which was equipped as in Example 1. Then, 15.8 gms. of the silane was placed in a glass vial and there was added 0.5 gm. of Vazo 64 catalyst. The catalyst did not completely dissolve and an additional 2 gms. of silane was added to the vial to help dissolve the catalyst. Thereafter, 58.1 gms. of allyl thiourea was added to the flask, in toto, and the catalyst/silane mixture was placed in an addition funnel. The flask was heated to about 85° C. which caused the solid allylurea to melt. The Vazo/silane mixture was then added at a fast dropwise rate whereupon the temperature dropped rapidly and, at the end of the addition, the temperature began to increase and it finally reached 95° C. The temperature was held at 90°-95° C. for 5 hours. During this time, the reaction material colored from yellow to orange to brown. An iodine titration showed the reaction had progressed about 42%. Another 0.3 gm. of catalyst was added and the reaction was heated for another 8 hours at about 90°-95° C. at which time a titration showed the reaction had gone to about 56% completion.

EXAMPLE 5

Preparation of

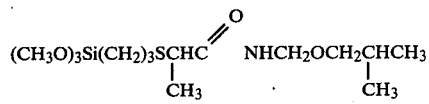

The reaction was carried out approximately as set forth in Example 1. Mercaptopropyltrimethoxysilane, 105 gms., was reacted with 78.6 gms. of isobutoxymethylacrylamide by adding the isobutoxymethylacrylamide to the silane at 100° C. over a period of about 2 hours and then the reaction was heated an additional 5 hours. A titration indicated that the reaction was 86% complete.

EXAMPLE 6

Preparation of

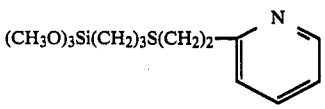

One hundred grams of mercaptopropyltrimethoxysilane and 0.45 gm. of Vazo 64 were placed in a flask equipped as in Example 1 above. The mixture was heated to 100° C. and vinyl pyridine was added from an addition funnel (52.5 gms.). The temperature rose to 120° C. whereupon the heating was discontinued and the temperature was reduced to about 100° C. The addition required about 45 minutes. After 2½ hours of heating, the contents of the flask were golden brown in color. The reaction was heated at 100° C. for about 6 hours. The reaction had proceeded to about 96% completion as indicated by a titration for the residual —SH.

The reaction product was analyzed by H'NMR analysis and the analysis was consistent with the structure

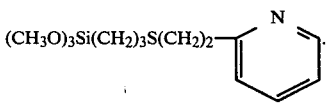

EXAMPLE 7

Preparation of

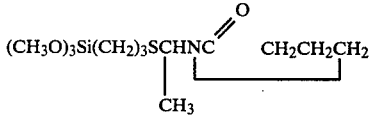

using a peroxide catalyst as a free radical source

Into a 500 ml., 3-necked flask equipped as in Example 1, there was added 105 gms. of mercaptopropyltrimethoxysilane and 0.5 gm. of benzoyl peroxide. Into an addition funnel there was poured 55.6 gms. of vinyl pyrrolidone. The flask was heated to about 90° C. and the addition was begun. The addition took about one hour and the contents of the flask colored from clear yellow to clear yellow brown. After the addition was complete, the contents were heated for four additional hours at about 90° C. and the contents continued to color a darker brown. An iodine titration indicated that the reaction had progressed to essentially 100% completion.

EXAMPLE 8

The preparation of

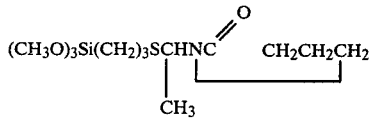

without the addition of a free radical catalyst

Mercaptopropyltrimethoxysilane, 105 gms., was placed in a 500 ml., 3-necked flask and equipped as in Example 1. Vinyl pyrrolidone, 55.6 gms., was poured into the addition funnel. The silane was heated to 100° C. and the pyrrolidone was added thereto with an exotherm which was controlled to 95°-105° C. over one hour. At the end of this time, an iodine titration indicated the reaction was about 95% complete. The reaction was heated for about 2½ additional hours to ensure completion of the reaction.

EXAMPLE 9

Tintability of an abrasion resistant coating using

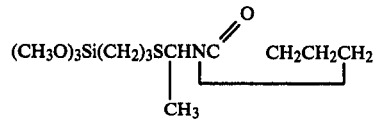

A commercial abrasion resistant coating resin prepared according to Example 1 of U.S. Pat. No. 3,986,997 and available from Dow Corning Corporation, Midland, Michigan, as Q9-6312 abrasion resistant coating resin, was used in the following manner with the tintable adduct prepared as in Example 1 herein. The tintable adduct at 100% solids was diluted with isopropanol/butanol (50/50 weight percent) to 45 weight percent solids. One hundred grams of this diluted solution was added to 400 gms. of the Q9-6312 resin. The pH of the mixture was adjusted to 4.7 by the use of acetic acid. A trace of a surfactant was added to help the coating wet out on the surface.

Three polycarbonate plastic panels (4"×4") were vapor degreased to clean them, and then they were heat annealed at 125° C. for two hours in an air circulating oven. The panels were then flow coated with the coating resin prepared above which contained the tintable adduct and cured in an air circulating oven at 125° C. for 16 hours. The panels were cooled and one panel was tested for adhesion of the coating and for abrasion resistance. Two of the panels were tinted by using a brown dye manufactured by Brain Power, Inc., Miami, FL, USA, and named Sun Brown.

The dye bath was heated to 95° C. and the panels were immersed in the bath for 15 minutes and removed. The coating dyed a greenish-brown color. Polycarbonate panels coated with the adduct-modified Q9-6312 without tinting have a light transmission of 90.4%. The tinted panel (average of two panels) light transmission was 80.5% or a reduction of 10% in light transmission. A sample of the Q9-6312 without the adduct would not tint at all, even on prolonged immersion in the heated dye bath. The adhesion of the coating containing the adduct, before tinting, was 100% and after tinting, the adhesion was still 100%. The % Δ Haze abrasion reading was 5.5%.

EXAMPLE 10

An abrasion resistant coating resin was prepared according to the general procedure set forth in U.S. Pat. No. 3,986,997. This resin composition was combined in various proportions with various adducts set forth in Table I such that the final resin composition was about 34% solids, wherein the solids consisted of about 54 weight percent $SiO_2$, 16 weight percent $CH_3SiO_{3/2}$ and 30 weight percent adduct as the silsesquioxane i.e. $RSiO_{3/2}$. The pH of all of the resin samples was adjusted to 4.7 prior to curing on the panels. Polycarbonate panels (4"×4") were flow coated with the resin compositions and cured at 125° C. for 16 hours in an air circulating oven. When removed from the oven and cooled, Sample 4 panels crazed badly.

The panels were then tinted using the brown dye bath, as in Example 9, for 15 minutes.

The results are on Table I.

The silane, in the trialkoxy form, is combined with the aqueous colloidal silica and mixed while hydrolysis takes place for about 90 minutes. The composition is then diluted with IPA/BuOH (2:1 weight ratio), and the adduct was added with stirring which was continued for two hours after the addition. The catalyst was then added. Each resin was flow coated onto B 4"×4"

TABLE I

Results of Tinting on Coated Polycarbonate Panels

| Sample No. | $ASiO_{3/2}$ where A is — | Tintability % Transmission Pretint | Tintability % Transmission Posttint | Abrasion Resistance % Δ Haze Pretint | Abrasion Resistance % Δ Haze Posttint | % Adhesion Pretint | % Adhesion Posttint |
|---|---|---|---|---|---|---|---|
| 1 | No adduct | 90.4 | 90.4 (No tintability) | 2.0 | 2.0 | 100 | 100 |
| 2 | $(CH_2)_3SCHNC(=O)$—$CH_2CH_2CH_2$ (ring), with $CH_3$ | 89.4 | 50.2 | 8.4 | 9.5 | 100 | 100 |
| 3 | $(CH_2)_3SCC(=O)NH_2$, with $(CH_3)_2$ | 89.4 | 68.3 | 4.9 | 4.0 | 0 | 0 |
| 4 | $(CH_2)_3SCHCH_2NHCNH_2$ (C=S), with $CH_3$ | 88.9 | 67.3 | 5.5 | 3.5 | 0 | 0 |
| 5 | $(CH_2)_3SCHC(=O)N(CH_3)_2$, with $CH_3$ | 89.5 | 43.9 | 11.3 | 6.1 | 100 | 100 |

EXAMPLE 11

This example illustrates the versatility of utility of the adducts of this invention in various siloxane resins containing $SiO_2$. In this case, R in the $RSiO_{3/2}$ is changed to change the type of resin obtained.

polycarbonate panels, air dried and cured 16 hours at 125° C. Three panels were coated with each resin. The adduct used in each case was that prepared as in Example 1. (See Table II for resin compositions and Table III for results of adhesion and tinting). The dye procedure and bath was the same as used in Example 9.

TABLE II

Composition Data for Resin Compositions

| Ref. | Silane Type/gms. | $SiO_2$/gms. | $CH_3COOH$/gms. | Adduct/gms. | Solvent/gms. | Catalyst/gms. |
|---|---|---|---|---|---|---|
| A | Vinyltrimethoxysilane | (11.8) | 67.9 | 1.6 | 16.8 | 39.0 | 1.29 |
| B | $(CH_3O)_3Si(CH_2)_3OC(=O)$—$C(CH_3)=CH$ | (8.7) | 67.9 | 1.5 | 16.8 | 43.0 | 1.29 |
| C | $(CH_3O)_3Si(CH_2)_3Cl$ | (9.7) | 67.9 | 1.6 | 16.8 | 42.0 | 1.29 |
| D | $(CH_3O)_3SiCH_3$ | (12.8) | 67.9 | 1.7 | 16.8 | 39.0 | 1.29 |

The colloidal silica used in this example is a basic colloidal dispersion of 13–14 millimicrons silica (pH) 9.8, $Na_2O$ content of 0.32%). The adducts were added as 100% solids reaction products. Sodium acetate catalyst was also added to the final composition before curing the resin on the panels.

A base resin is prepared by adding each silane to colloidal silica at weight ratios of 78.5:21.5 $SiO_2$ to silane. This material is then diluted with isopropanol/butanol (IPA/BuOH) solvent (1:1 weight ratio) to obtain the final composition. One sample will illustrate the procedure.

TABLE III

Results on Tintability and Adhesion of Various Siloxane/$SiO_2$ Resin

| Ref. | Tintability % Transmission | Abrasion Resistance % Δ Haze | % Adhesion Pretint | % Adhesion Posttint |
|---|---|---|---|---|
| A | 46.9 | 19.0 | 100 | 0 |
| B | 10.4 | 25.4 | 100 | — |
| C | 23.6 | 27.6 | 100 | — |
| D | 65.0 | 6.5 | 100 | 90 |

EXAMPLE 12

The effects on adhesion and tintability while varying the quantity of an inventive adduct Inventive adduct was prepared as in Example 1. This adduct was diluted with IPA/BuOH (1:1) to 35 weight percent solids. This material was labeled "Component A". "Component B" is the commercial abrasion resistant coating referred to earlier in this application as Q9-6312 and is also 35 weight percent solids. These resins were blended to give varying ratios of A to B. The blends were then coated on polycarbonate plastic panels and tinted. Adhesion, tintability, and abrasion resistance were tested. A mixture of $CH_3COOH$ and $NaOOCCH_3$, 50:50 weight ratio, was added to adjust pH to 4.7.

| Sample Ref. | Component A gms. | Component B gms. | $CH_3COOH + NaOOCCH_3$/gms. |
|---|---|---|---|
| 1 | 10 | 90 | 0.2 |
| 2 | 20 | 80 | 0.4 |
| 3 | 30 | 70 | 0.6 |
| 4 | 40 | 60 | 0.8 |
| 5 | 50 | 50 | 1.0 | see Table IV for test results on these materials.

TABLE IV

Results of Adhesion/Tintability/Abrasion Resistance of Example 12 Resin Compositions

| Sample Ref. | Abrasion Resistance/% Δ Haze | % Adhesion Pretint | % Adhesion Posttint | Tintability % Transmission |
|---|---|---|---|---|
| 1 | 3.7 | 100 | 100 | 89.0 |
| 2 | 7.0 | 100 | 100 | 84.0 |
| 3 | 13.8 | 100 | 100 | 64.6 |
| 4 | 20.5 | 100 | 100 | 46.4 |
| 5 | 37.5 | 100 | 100 | 37.0 |

EXAMPLE 13

Preparation of $(CH_3O)_3Si(CH_2)_3SCH_2CH_2CH_2NHCONH_2$ 70 grams of mercaptopropyltrimethoxy silane and 35.5 gms. of allylurea were weighed into a flask equipped as in Example 1. The contents of the flask were heated to about 90° C. and 0.3 gm. of Vazo 64 was added. The temperature indicated an exotherm to about 145° C. which was controlled back down to about 100° C. for a total of 6½ hours and it was then cooled. Titration of a sample showed about 71% reaction of the mercaptan. The material was filtered. The proton NMR analysis showed a structure consistent with the title compound. There was unreacted allylurea present at less than 25%.

EXAMPLE 14

The following base resin was prepared. Eighty and eight-tenths grams of colloidal $SiO_2$ (as in Example 1); 15.2 grams of $CH_3Si(OCH_3)_3$ and 2 grams of $CH_3COOH$ were stirred together for one hour. 86.9 grams of isopropyl alcohol was added thereto along with 43.4 gms. of butanol. This material was stirred to homogenize and was then split into two equal quantities. One-half of this resin was combined with 9.8 gms. of the material from Example 13. The second one-half was combined with 9.2 gms. of the material from Example 6 and after stirring it gelled. A new resin was prepared and combined with ten gms. of the material from Example 6. About 630 ppm of sodium acetate in an isopropanol solution was added to each combination. The combination using the material from Example 13 was labeled A. The second combination using the material of Example 6 was labeled B.

A and B were flow coated on separate polycarbonate 4"×4" plastic panels which had been previously vapor degreased and heat annealed for two hours at 125° C. and cooled. After coating, the panels were air dried for about 15 minutes and then cured in an air circulating oven at 125° C. overnight. The panels were dyed using BPI Sun Brown dye at 90°–95° C. for 15 minutes. The results were as follows. A vinyl pyrrolidone adduct in the base resin of this example was prepared and was tested as Reference C.

| Ref. | % Adhesion Pretint | % Adhesion Posttint | % Δ Haze | % Light Transmission |
|---|---|---|---|---|
| A | 100 | 100 | 18.2 | 74.0 (30 min. immersion) |
| B | 100 | 100 | 44.2 | 51.0 |
| C | 100 | 100 | 30.0 | 73.6 |

EXAMPLE 15

The use of the inventive adduct in a commercial tintable coating to further reduce the light transmission A coating resin was prepared as shown in Example 2 of U.S. Pat. No. 4,073,967. This resin was divided into two equal portions. The portion that was used "as prepared" was designated A. The other half of the resin was combined with an adduct analogous to and prepared as in Example 1 in a quantity of 16 weight percent adduct.

These resins were coated on separate 4"×4" polycarbonate panels and air dried about 15 minutes and then cured overnight (about 16 hours) at 85° C. The panels were tinted as in Example 14 above. The Panel A had a light transmission of 35%. Panel B had a light transmission of less than 1%.

EXAMPLE 16

Effect of variation in the $SiO_2$ content of the coating resin on dyeability/tintability Five resins were prepared in which the $SiO_2$ content was varied. The resins were prepared by mixing methyltrimethoxysilane, colloidal silica (as in Example 1), acetic acid and water. After these materials were mixed and homogenized with stirring, a 50/50 weight ratio of isopropanol and butanol solvent was added to the resin. After continued stirring for a few minutes, the resins cleared and they were then stirred for three hours and there was added thereto an adduct prepared as in Example 1 and having the same chemical formula. The resins were allowed to stand overnight and about 600 ppm sodium acetate was added to each resin as a curing catalyst. The resin formulations can be found in the following table. EXAMPLE 16

| | The Resin Formulations | | | | | | |
|---|---|---|---|---|---|---|---|
| Ref. | gms. $CH_3Si(OCH_3)_3$ | gms. $SiO_2$ | gms. Acetic Acid | gms. $H_2O$ | gms. Solvent | gms. Adduct | Wt. % $SiO_2$ |
| A | 60.8 | 14.7 | 1.9 | 21.0 | 100 | 20 | 10 |

-continued

| | | | The Resin Formulations | | | | |
|---|---|---|---|---|---|---|---|
| Ref. | gms. $CH_3Si(OCH_3)_3$ | gms. $SiO_2$ | gms. Acetic Acid | gms. $H_2O$ | gms. Solvent | gms. Adduct | Wt. % $SiO_2$ |
| B | 40.6 | 44.1 | 1.7 | 0.0 | 91.5 | 20 | 30 |
| C | 20.3 | 73.4 | 1.7 | 0.0 | 82.6 | 20 | 50 |
| D | 5.1 | 95.6 | 2.0 | 0.0 | 73.3 | 20 | 65 |
| E | 0.0 | 102.3 | 2.0 | 0.0 | 73.7 | 20 | 70 |

These resins were flow coated on separate polycarbonate 4"×4" panels which had been vapor degreased and heat annealed at 125° C. and cooled before coating. The panels were cured about 16 hours in an air convection oven at 125° C.

The panels were tinted using the BPI Sun Brown for 15 minutes at 85° C. The results can be found in Table V.

TABLE V

Results of the Variability of the $SiO_2$ Content of the Base Resin

| Ref. | Average Coating Thickness/μ | % Δ Haze | % Adhesion | % Transmission Pretint | % Transmission Posttint |
|---|---|---|---|---|---|
| A | 5.0 | 15.5 | 100 | 89.1 | 85.4 |
| B | 4.6 | 9.5 | 100 | 89.0 | 82.3 |
| C | 4.2 | 7.4 | 100 | 89.0 | 76.6 |
| D | 2.9 | 20.8 | 100 | 88.7 | 64.2 |
| E | 2.0 | 23.7 | 100 | 88.5 | 25.0 |

In base resin coatings which contain colloidal silica, it is apparent that greater dyeability can be achieved by increasing the amount of $SiO_2$ in the base resin, but it should be observed that at about 65 weight percent the coatings start to soften.

EXAMPLE 17

Use of the invention adducts in a commercial silicone resin

Three resins were prepared according to Japanese Patent Publication Sho 51 (1976)-123280, Example 3 and Comparison Example 1, page 9 of the publication. The formulations were prepared by simple mixing as shown in the publication and they had the following formulations:

| (A) | Methyltrimethoxysilane (MTM) | 27 gms. |
|---|---|---|
| | Vinyltrimethoxysilane (VTM) | 38 gms. |
| | $CH_3COOH$ | 8 gms. |
| | 0.02 N HCl | 21 gms |
| | Na Acetate | 0.4 gms. |
| (B) | MTM | 27 gms. |
| | VTM | 38 gms. |
| | 0.02 N HCl | 21 gms. |
| | $CH_3COOH$ | 8 gms. |
| | Na Acetate | 0.4 gms. |
| | Ni (CO―CH$_3$)$_2$ · 4H$_2$O | 2.8 gms. |
| (C) | MTM | 27 gms. |
| | VTM | 25 gms. |
| | $CH_3COOH$ | 8 gms. |
| | 0.02 N HCl | 21 gms. |
| | Na Acetate | 0.4 gms. |
| | *Adduct | 13 gms. |

*The adduct had the same chemical structure as that prepared in Example 1 of this application.

Polycarbonate panels (4"×4") were vapor degreased and heat annealed at 125° C. and cooled before coating. Both acrylic plastic panels (Plexiglas ®G product of Rohm and Haas, Philadelphia, PA, USA) and polycarbonate panels (Lexan ® General Electric Co., Plastic Division, Pittfield, Mass., USA) (4"×4") were flow coated, air dried for 25 minutes and then cured in an air convection oven, the acrylic panels at 80° C. for 16 hours and the polycarbonate panels at 125° C. for 16 hours. The panels were all dyed using BPI Sun Brown at 85° C. for 15 minutes. The results are on Table VI.

TABLE VI

Results from Example 17

| Ref. | % Δ Haze Polycarbonate (PC) | % Δ Haze Acrylic (AC) | % Transmission PC | % Transmission AC | % Adhesion PC | % Adhesion AC |
|---|---|---|---|---|---|---|
| A | Crazed Badly | 25 | — | 75 | 0 | 100 |
| B | Crazed Badly | 25 | — | 72 | 0 | 100 |
| C | Crazed About 20% of Surface Area | 20 | — | 59 | 100 | 100 |

That which is claimed is:

1. A solid substrate coated with a composition of matter which is a silane having the general formula $(XO)_3SiRSR'$ wherein X is an alkyl radical of 1–4 carbon atoms, R is a divalent aliphatic hydrocarbon radical containing less than five carbon atoms and R' is selected from a group consisting of

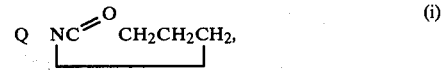

(i)

(ii)

(iii)

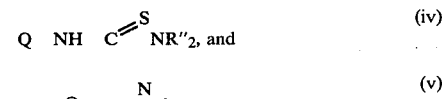

(iv)

(v)

wherein Q is a radical selected from a group consisting of —$CH_2CH_2$—, —$CH_2CH_2CH_2$—,

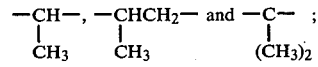

wherein in groups (iii) and (iv), R" is hydrogen or the methyl group and in group (ii), R" is hydrogen, the methyl group or the isobutoxymethyl group.

2. A solid substrate coated with a composition of matter which comprises
  (A) 1 to 50 weight percent, based on the weight of (A) and (B), of a silane having the general formula $(XO)_3SiRSR'$ wherein X is an alkyl radical of 1 to 4 carbon atoms, R is a divalent aliphatic hydrocarbon radical containing less then five carbon atoms and R' is selected from a group consisting of

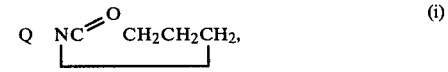

(i)

(ii)

-continued

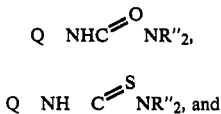

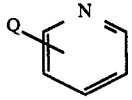

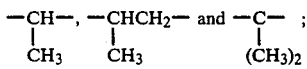

wherein Q is a radical selected from a group consisting of —CH$_2$CH$_2$—, —CH$_2$CH$_2$CH$_2$—, $$-\underset{\underset{CH_3}{|}}{CH}-,\ -\underset{\underset{CH_3}{|}}{CH}CH_2- \text{ and } -\underset{\underset{(CH_3)_2}{|}}{C}-\ ;$$

wherein in groups (iii) and (iv), R″ is hydrogen or the methyl group and in group (ii), R″ is hydrogen, the methyl group or the isobutoxymethyl group, and (B) 99 to 50 weight percent, based on the weight of (A) and (B), of a curable resin compatible with component (A).

3. A method of rendering a substrate antistatic by coating said substrate with a composition of matter which is a silane having the general formula (XO)$_3$SiRSR′ wherein X is an alkyl radical of 1-4 carbon atoms, R is a divalent aliphatic hydrocarbon radical containing less than five carbon atoms and R′ is selected from a group consisting of

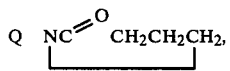

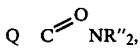

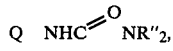

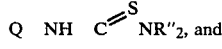

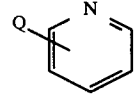

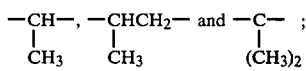

wherein Q is a radical selected from a group consisting of —CH$_2$CH$_2$—, —CH$_2$CH$_2$CH$_2$—, $$-\underset{\underset{CH_3}{|}}{CH}-,\ -\underset{\underset{CH_3}{|}}{CH}CH_2- \text{ and } -\underset{\underset{(CH_3)_2}{|}}{C}-\ ;$$

wherein in groups (iii) and (iv), R″ is hydrogen or the methyl group and in group (ii), R″ is hydrogen, the methyl group or the isobutoxymethyl group.

4. A method of rendering a substrate antistatic by coating said substrate with a composition of matter which comprises (A) 1 to 50 weight percent, based on the weight of (A) and (B), of a silane having the general formula (XO)$_3$SiRSR′ wherein X is an alkyl radical of 1 to 4 carbon atoms, R is a divalent aliphatic hydrocarbon radical containing less than five carbon atoms and R′ is selected from a group consisting of

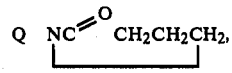

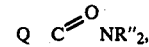

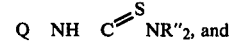

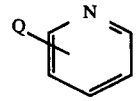

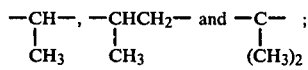

wherein Q is a radical selected from a group consisting of —CH$_2$CH$_2$—, —CH$_2$CH$_2$CH$_2$—, $$-\underset{\underset{CH_3}{|}}{CH}-,\ -\underset{\underset{CH_3}{|}}{CH}CH_2- \text{ and } -\underset{\underset{(CH_3)_2}{|}}{C}-\ ;$$

wherein in groups (iii) and (iv), R″ is hydrogen or the methyl group and in group (ii), R″ is hydrogen, the methyl group or the isobutoxymethyl group, and (B) 99 to 50 weight percent, based on the weight of (A) and (B), of a curable resin compatible with component (A).

5. A method of inhibiting fog on a substrate by coating said substrate with a composition of matter which is a silane having the general formula (XO)$_3$SiRSR′ wherein X is an alkyl radical of 1-4 carbon atoms, R is a divalent aliphatic hydrocarbon radical containing less than five carbon atoms and R′ is selected from a group consisting of

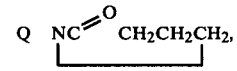

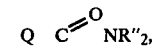

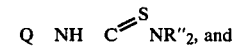

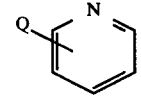

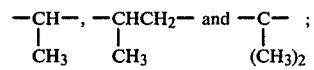

wherein Q is a radical selected from a group consisting of —CH$_2$CH$_2$—, —CH$_2$CH$_2$CH$_2$—, $$-\underset{\underset{CH_3}{|}}{CH}-,\ -\underset{\underset{CH_3}{|}}{CH}CH_2- \text{ and } -\underset{\underset{(CH_3)_2}{|}}{C}-\ ;$$

wherein in groups (iii) and (iv), R″ is hydrogen or the methyl group and in group (ii), R″ is hydrogen, the methyl group or the isobutoxymethyl group.

6. A method of inhibiting fog on a substrate by coating said substrate with a composition of matter which comprises (A) 1 to 50 weight percent, based on the weight of (A) and (B), of a silane having the general formula $(XO)_3SiRSR'$ wherein X is an alkyl radical of 1 to 4 carbon atoms, R is a divalent aliphatic hydrocarbon radical containing less then five carbon atoms and R' is selected from a group consisting of

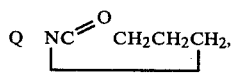 (i)

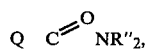 (ii)

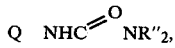 (iii)

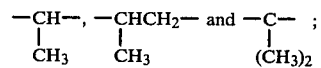 (iv)

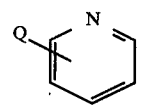 (v)

wherein Q is a radical selected from a group consisting of —CH$_2$CH$_2$—, —CH$_2$CH$_2$CH$_2$—, $$-\underset{CH_3}{\overset{|}{C}H}-,\ -\underset{CH_3}{\overset{|}{C}H}CH_2-\ \text{and}\ -\underset{(CH_3)_2}{\overset{|}{C}}-\ ;$$

wherein in groups (iii) and (iv), R" is hydrogen or the methyl group and in group (ii), R" is hydrogen, the methyl group or the isobutoxymethyl group, and (B) 99 to 50 weight percent, based on the weight of (A) and (B), of a curable resin compatible with component (A).

* * * * *